(12) United States Patent
Benkowski et al.

(10) Patent No.: US 8,323,173 B2
(45) Date of Patent: Dec. 4, 2012

(54) METHOD AND SYSTEM FOR PHYSIOLOGIC CONTROL OF AN IMPLANTABLE BLOOD PUMP

(75) Inventors: Robert J Benkowski, Houston, TX (US); Gino F Morello, Leonia, NJ (US)

(73) Assignee: MicroMed Technology, Inc., Houston, TX (US)

( * ) Notice: Subject to any disclaimer, the term of this patent is extended or adjusted under 35 U.S.C. 154(b) by 1796 days.

(21) Appl. No.: 10/501,112

(22) PCT Filed: Jan. 7, 2003

(86) PCT No.: PCT/US03/00273
§ 371 (c)(1),
(2), (4) Date: Jul. 7, 2004

(87) PCT Pub. No.: WO03/057280
PCT Pub. Date: Jul. 17, 2003

(65) Prior Publication Data
US 2005/0131271 A1    Jun. 16, 2005

Related U.S. Application Data

(60) Provisional application No. 60/346,721, filed on Jan. 7, 2002.

(51) Int. Cl.
*A61M 1/12* (2006.01)
(52) U.S. Cl. .................................. 600/17; 623/3.28
(58) Field of Classification Search ............. 600/17; 623/3.28
See application file for complete search history.

(56) References Cited

U.S. PATENT DOCUMENTS

| | | | |
|---|---|---|---|
| 3,911,897 A * | 10/1975 | Leachman, Jr. ............... | 600/17 |
| 4,221,543 A | 9/1980 | Cosentino et al. | |
| 4,363,609 A | 12/1982 | Cosentino et al. | |
| 4,465,063 A * | 8/1984 | Nielsen et al. ................ | 600/16 |
| 4,557,673 A | 12/1985 | Chen et al. | |
| 4,578,077 A | 3/1986 | Joh | |
| 4,692,145 A | 9/1987 | Weyant | |
| 4,782,817 A * | 11/1988 | Singh et al. ................... | 600/17 |
| 4,957,504 A | 9/1990 | Chardack | |
| 5,041,086 A | 8/1991 | Koenig et al. | |
| 5,108,360 A * | 4/1992 | Tachi ............................. | 600/16 |
| 5,113,869 A | 5/1992 | Nappholz et al. | |

(Continued)

FOREIGN PATENT DOCUMENTS

WO    8800378 A1    6/1988
(Continued)

OTHER PUBLICATIONS

Supplementary European Search Report for Corresponding European Patent Application No. 03703701.7.

*Primary Examiner* — George Evanisko
(74) *Attorney, Agent, or Firm* — Sutton McAughan Deaver PLLC

(57) ABSTRACT

A physiologic control method and system for an implantable blood pump includes operating the pump at a predetermined speed and monitoring the patient's diastolic pump flow rate. The predetermined speed is varied in response to the diastolic pump flow rate. The pump speed may further be adjusted in response to the patient's heart rate. The speed may be increased and decreased in response to corresponding changes in the diastolic pump flow rate, and increased in response to an increase in heart rate.

20 Claims, 6 Drawing Sheets

U.S. PATENT DOCUMENTS

| | | | |
|---|---|---|---|
| 5,511,958 A | 4/1996 | Chen et al. | |
| 5,527,159 A | 6/1996 | Bozeman, Jr. et al. | |
| 5,569,156 A | 10/1996 | Mussivand | |
| 5,599,173 A | 2/1997 | Chen et al. | |
| 5,713,856 A | 2/1998 | Eggers et al. | |
| 5,888,242 A | 3/1999 | Antaki et al. | |
| 5,947,892 A | 9/1999 | Benkowski et al. | |
| 5,975,126 A | 11/1999 | Bump et al. | |
| 6,048,363 A * | 4/2000 | Nagyszalanczy et al. | 623/3.13 |
| 6,066,086 A * | 5/2000 | Antaki et al. | 600/17 |
| 6,183,412 B1 | 2/2001 | Benkowski et al. | |
| 6,395,027 B1 * | 5/2002 | Snyder | 623/3.28 |
| 6,605,032 B2 | 8/2003 | Benkowski et al. | |
| 6,623,420 B2 * | 9/2003 | Reich et al. | 600/17 |
| 2003/0069465 A1 | 4/2003 | Benkowski et al. | |
| 2004/0152944 A1 * | 8/2004 | Medvedev et al. | 600/17 |

FOREIGN PATENT DOCUMENTS

| | | |
|---|---|---|
| WO | 0019097 A1 | 4/2000 |
| WO | 0044417 | 8/2000 |
| WO | 0172352 | 10/2001 |
| WO | 2004054641 A1 | 7/2004 |

* cited by examiner

METHOD AND SYSTEM FOR PHYSIOLOGIC CONTROL OF AN IMPLANTABLE BLOOD PUMP

This application claims the benefit of U.S. Provisional Application No. 60/346,721, filed on Jan. 7, 2002, the entire contents of which is incorporated by reference.

BACKGROUND OF THE NVETION 1. FIELD OF THE INVENTION

The invention relates generally to implanted or implantable blood pump systems, and more specifically, to a method and system for physiologic control of such pumps. 2. DESCRIPTION OF RELATED ART Generally, implantable blood pump systems are employed in either of two circumstances. First an implantable blood pump may completely replace a human heart that is not functioning properly, or second, an implantable blood pump may boost blood circulation in patients whose heart is still functioning although pumping at an inadequate rate.

For example, U.S. Pat. No. 6,183,412, which is commonly assigned and incorporated herein by reference in its entirety, discloses a ventricle assist device (VAD) commercially referred to as the "DeBakey VAD®." The VAD is a miniaturized continuous axial-flow pump designed to provide additional blood flow to patients who suffer from heart disease. The device is attached between the apex of the left ventricle and the aorta.

Known implantable blood pump systems typically are controlled in an open loop fashion where a predetermined speed is set and the flow rate varies according to the pressure differential across the pump. The pump itself may be controlled in a closed loop fashion, wherein the actual pump speed is fed back to a motor controller that compares the actual speed to the desired predetermined speed and adjusts the pump accordingly. However, prior art closed loop control systems—varying the pump speed in response to a monitored physiologic parameter—have largely been unsatisfactory.

For example, some systems have attempted to use a patent's heart rate, or pulse, as a physiologic control trigger—the pump speed set point is varied in response to the patient's heart rate . Other systems attempt to vary the pump speed based on the variation of the VAD pump's flow or current signals with respect to the signal's mean value or with respect to pump speed. For example, a "pulsatility index" is derived $$\left(\text{e.g. } \frac{Signal_{MAX} - Signal_{MIN}}{Signal_{MEAN}}\right)$$

and compared to a predetermined threshold and the pump speed is varied accordingly.

Unfortunately, these physiologic control methods have not provided an adequate closed loop control parameter, as it appears that known physiologic control parameters such as these do not necessarily vary proportionally to a patient's level of activity—i.e., the patient's demand for increased blood flow. Further, while a patient's heart rate may increase during exercise, heart rate may be controlled by other factors, such as medication or a pacing device. Still further, the patient may not have significant native heart rate function, preventing the heart rate from increasing in response to the body's demand for increased blood flow. Moreover, there exists some evidence that a patient's heart rate may decrease as the pump's speed is increased. Hence, heart rate alone may not provide a satisfactory physiologic control parameter.

The present invention addresses shortcomings associated with the prior art.

SUMMARY OF THE INVETION

Aspects of the present invention concern a physiologic control system and method for a blood pump system such as a VAD system. The pump system includes, for example, an implantable pump such as a VAD and a controller for controlling the pump. The system may firther include an implantable flow measurement device. The control method includes operating the pump at a predetermined speed and monitoring the patient's diastolic VAD flow rate. In exemplary embodiments, the peak diastolic VAD flow rate, average diastolic VAD flow rate, and/or the average peak diastolic VAD flow rate is monitored. The predetermined speed is varied in response to the diastolic VAD flow rate. The pump speed may further be adjusted in response to the patient's heart rate. In certain embodiments, the speed is increased and decreased in response to corresponding changes in the diastolic VAD flow rate.

BRIEF DESCRIPTION OF THE DRAWINGS

Other objects and advantages of the invention will become apparent upon reading the following detailed description and upon reference to the drawings in which.

Figure 1:
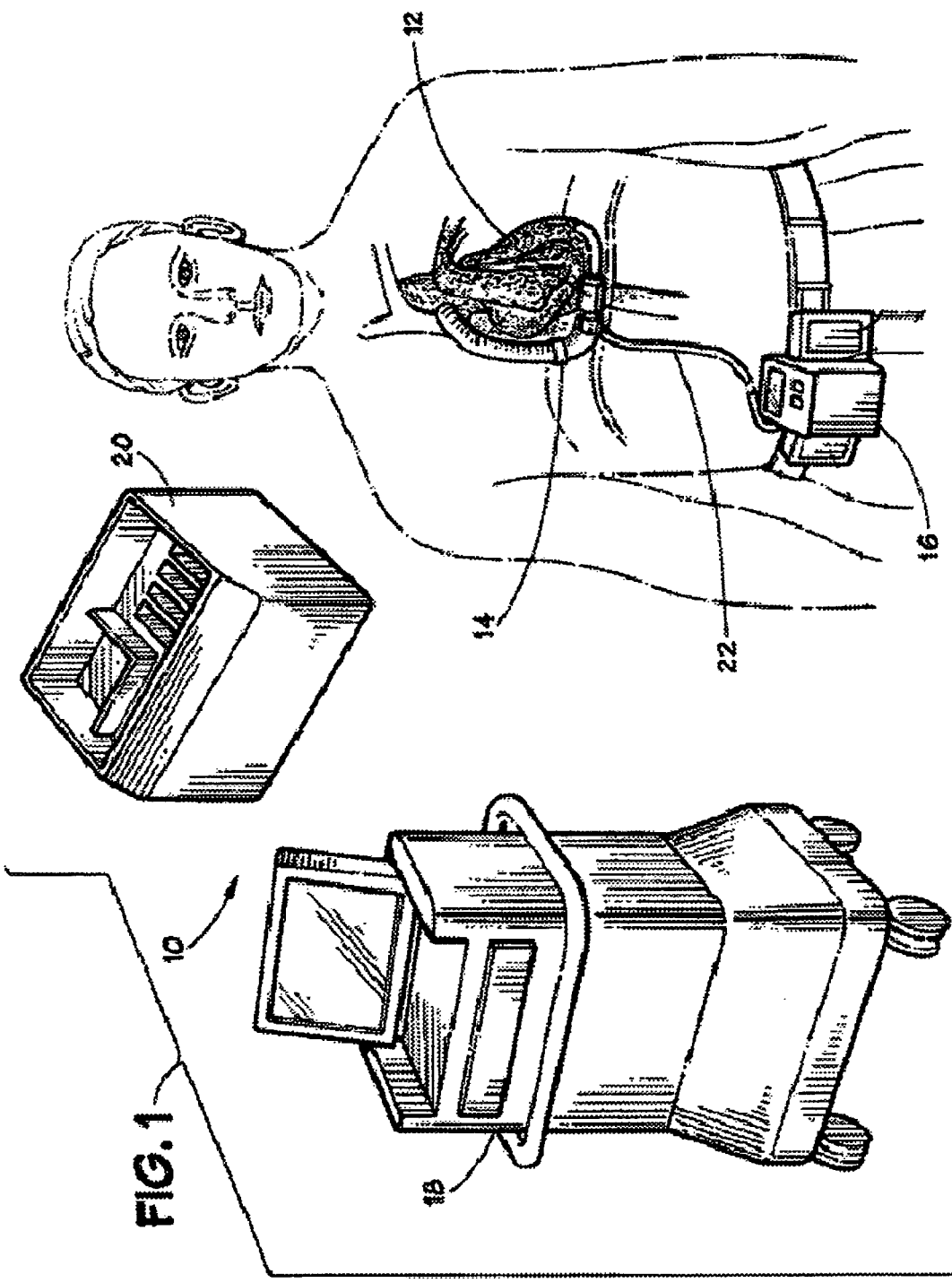
FIG. 1 schematically illustrates various components of an implantable pump system in accordance with embodiments of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVETION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning to the figures, FIG. 1 illustrates a ventricular assist device (VAD) system 10 such as disclosed in U.S. Pat. No. 6,183,412, which is commonly assigned and incorporated herein by reference in its entirety. The VAD system 10 includes components designed for implantation within a human body and components external to the body. Implantable components include a rotary pump 12 and a flow sensor 14. The external components include a portable controller module 16, a clinical data acquisition system (CDAS) 18, and a patient home support system (PHSS) 20. The implanted components are connected to the controller module 16 via a percutaneous cable 22.

Figure 2:
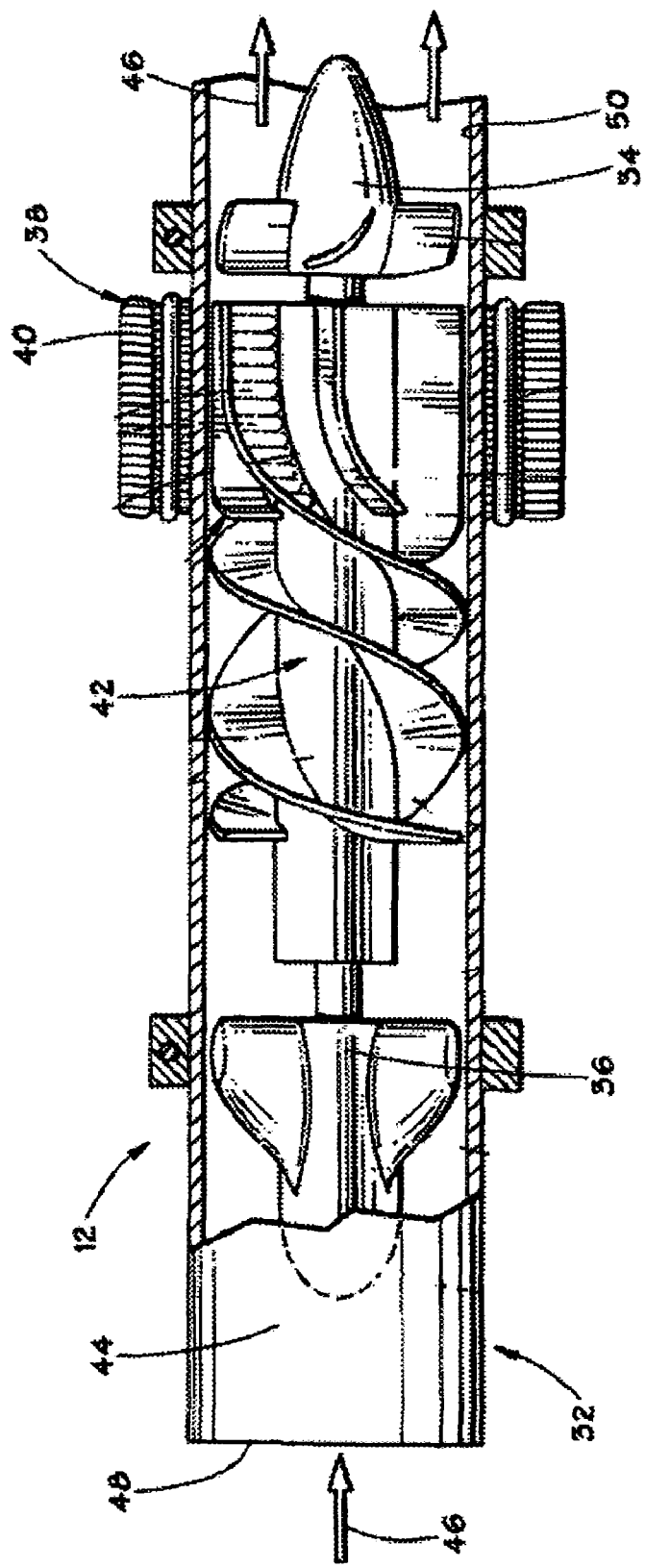
FIG. 2 is a cross-section view of an exemplary implantable pump in accordance with embodiments of the present invention.

The VAD System 10 may incorporate an implantable continuous-flow blood pump, such as the various embodiments of axial flow pumps disclosed in U.S. Pat. No. 5,527,159 or in U.S. Pat. No.5,947,892, both of which are incorporated herein by reference in their entirety. An example of a blood pump suitable for use in an embodiment of the invention is illustrated in FIG. 2. The exemplary pump 12 includes a pump housing 32, a diffuser 34, a flow straightener 36, and a brushless DC motor 38, which includes a stator 40 and a rotor 42. The housing 32 includes a flow tube 44 having a blood flow path 46 there through, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotating magnetic field to produce rotary motion.

Figure 3:
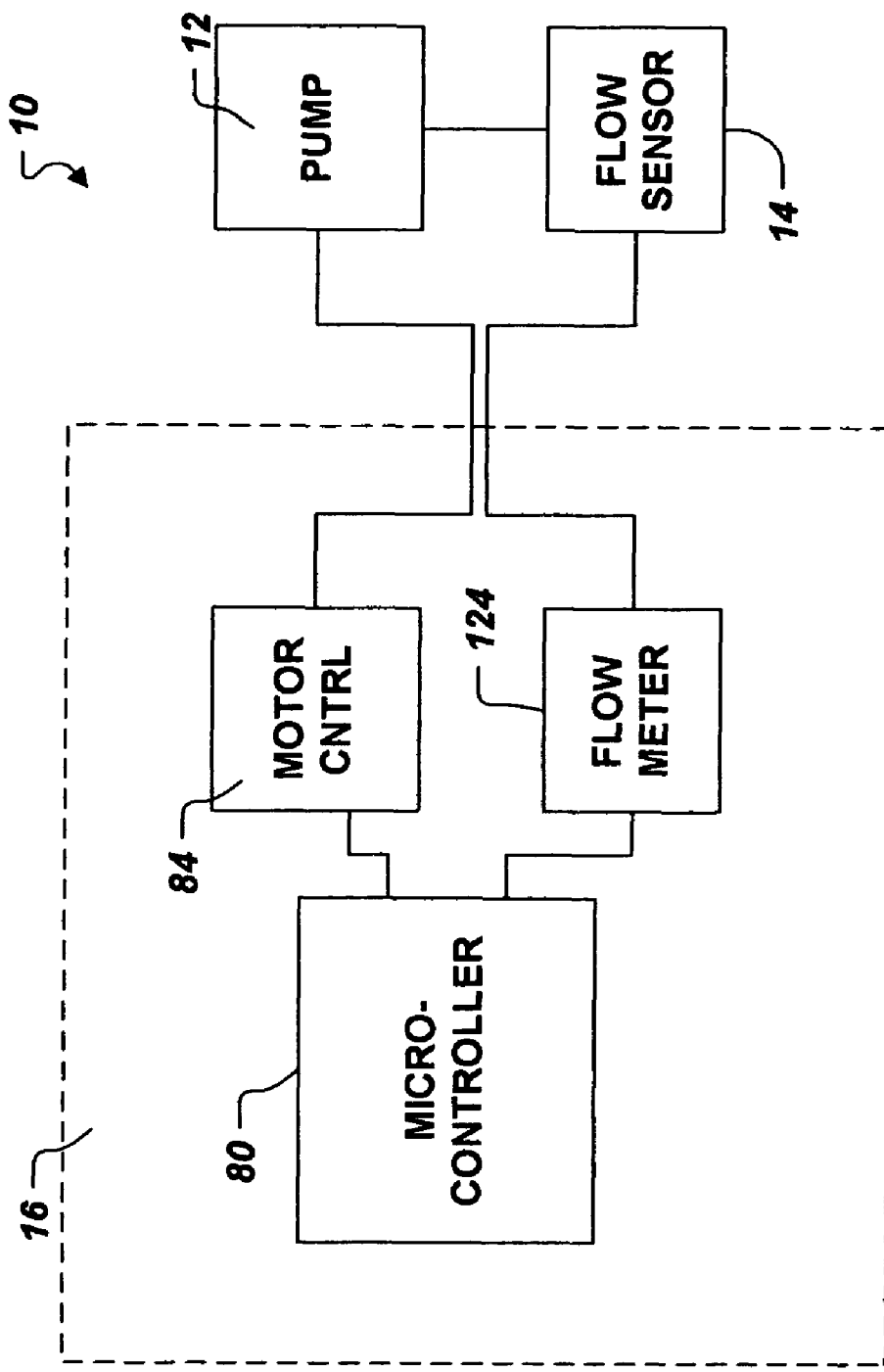
FIG. 3 is a block diagram illustrating aspects of a controller module in accordance with embodiments of the present invention.

FIG. 3 conceptually illustrates aspects of the pump system 10. More specifically, portions of the controller module 16 and the pump 12 are shown. The controller module 16 includes a processor, such as a microcontroller 80, which in one embodiment of the invention is a model PIC16C77 microcontroller manufactured by Microchip Technology. The microcontroller 80 includes a multiple channel analog to digital (A/D) converter, which receives indications of motor parameters from the motor controller 84. Thus, the controller module 16 may monitor parameters such as motor current, the VAD flow rate, and motor speed.

The embodiment shown in FIG. 3 further includes an integral flow meter 124. At least one flow sensor 14 is implanted down stream of the pump 12. Alternately, a flow sensor 14 may be integrated with the pump 12. The flow meter 124 is coupled between the implanted flow sensor 14 and the microcontroller 80. The flow meter 124 receives data from the flow sensor 14 and outputs flow rate data to the microcontroller 80, allowing the system to monitor instantaneous flow rate.

Since the implanted flow sensor 14 is coupled to the flow meter 124 of the controller module 16, a true measure of system performance (flow rate) is available for analysis, in addition to pump parameters such as motor speed and current (power). Further, since the flow meter 124 is an integral component of the controller module 16, VAD flow may be displayed on the controller module display and VAD flow rate data may be saved in the controller module memory.

In exemplary embodiments of the invention, the motor controller 84 comprises a MicroLinear ML425 Motor Controller provided by Fairchild Semiconductor. The operation of the brushless DC motor 38 of the present invention requires that current be applied in a proper sequence to the stator windings 52 to create the rotating field. Two stator windings 52 have current applied to them at any one time, and by sequencing the current on and off to the respective stator windings 52, the rotating magnetic field is produced. In an embodiment of the invention, the motor controller 84 senses back electromotive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 integrated into the rotor of the brushless DC motor 38, a voltage is induced. The voltage will increase with rotor speed 42. It is possible to sense this voltage to determine the rotor 42 position in one of the three stator windings 52 because only two of the motor's windings 52 are activated at any one time.

An alternative method of detecting the rotor 42 position relative to the stator 40 for providing the proper stator winding 52 excitation current sequence is to use a position sensor, such as a Hall Effect sensor. Implementing aspects of the present invention using a motor with rotor position sensors, rather than a sensorless motor, would be a routine undertaking for one skilled in the art having the benefit of this disclosure. However, adding additional components, such as Hall Effect sensors, requires additional space, which is limited in any implanted device application. Further, using a position detection device adds sources of system failures.

The actual pump speed is determined and fed back to the controller module 16, which compares the actual speed to a desired predetermined speed and adjusts the pump 12 accordingly. In accordance with certain embodiments of the invention, the pump 12 is controlled in a closed loop fashion wherein the desired pump speed is varied for events such as sleeping, normal activity or high energy exertion.

The contraction phase of the heart beat is referred to as systole, the relaxation phase is referred to as diastole. Thus, the systolic VAD flow is the maximum VAD flow rate, while the diastolic VAD flow rate is the minimum VAD flow rate. It has been determined (empirically) that a patient's diastolic VAD flow rate significantly increases at the onset of exercise, and decreases at the conclusion of exercise. In comparison, the systolic VAD flow rate, for example, remains relatively constant at the onset and conclusion of exercise. Thus, in certain embodiments of the invention, the pump speed is adjusted in response to changes in the diastolic VAD flow rate.

The contraction phase or pumping phase of the cardiac cycle is referred to as systole, the relaxation phase or filling phase is referred to as diastole. In healthy, non-VAD patients, there is positive blood flow, from the left ventricle through the aortic valve, during systole and no blood flow, from the left ventricle through the aortic valve, during diastole. However, in patients who have been implanted with a left VAD there is generally positive flow through the VAD during both systole and diastole. This is because the implanted continuous flow VAD essentially adds a constant positive flow offset to the native heart's pulsatile flow contribution.

Therefore, the conventional definitions for systolic flow and diastolic flow must be modified to make them applicable to patients implanted with left VADs. Thus, the systolic flow rate is considered herein as the flow contribution above the mean flow rate value, while the diastolic VAD flow rate is considered herein as the VAD flow contribution below the mean VAD flow rate. Peak systolic VAD flow rate is considered herein to be the maximum VAD flow rate value in the VAD flow rate waveform in one cardiac cycle and average peak systolic VAD flow rate is the average value of multiple peak systolic VAD flow rate values over several cardiac cycles. Similarly, peak diastolic VAD flow rate is considered herein to be the minimum VAD flow rate value in the VAD flow rate waveform in one cardiac cycle and average peak diastolic VAD flow rate is the average value of multiple peak diastolic VAD flow rate values over several cardiac cycles.

It has been determined that a patient's peak diastolic VAD flow rate or average peak diastolic VAD flow rate significantly increases at the onset of exercise, and decreases at the conclusion of exercise. Thus, in certain embodiments of the invention, the pump speed is adjusted in response to changes in the peak diastolic VAD flow rate or average peak diastolic VAD flow rate.

Figure 4:
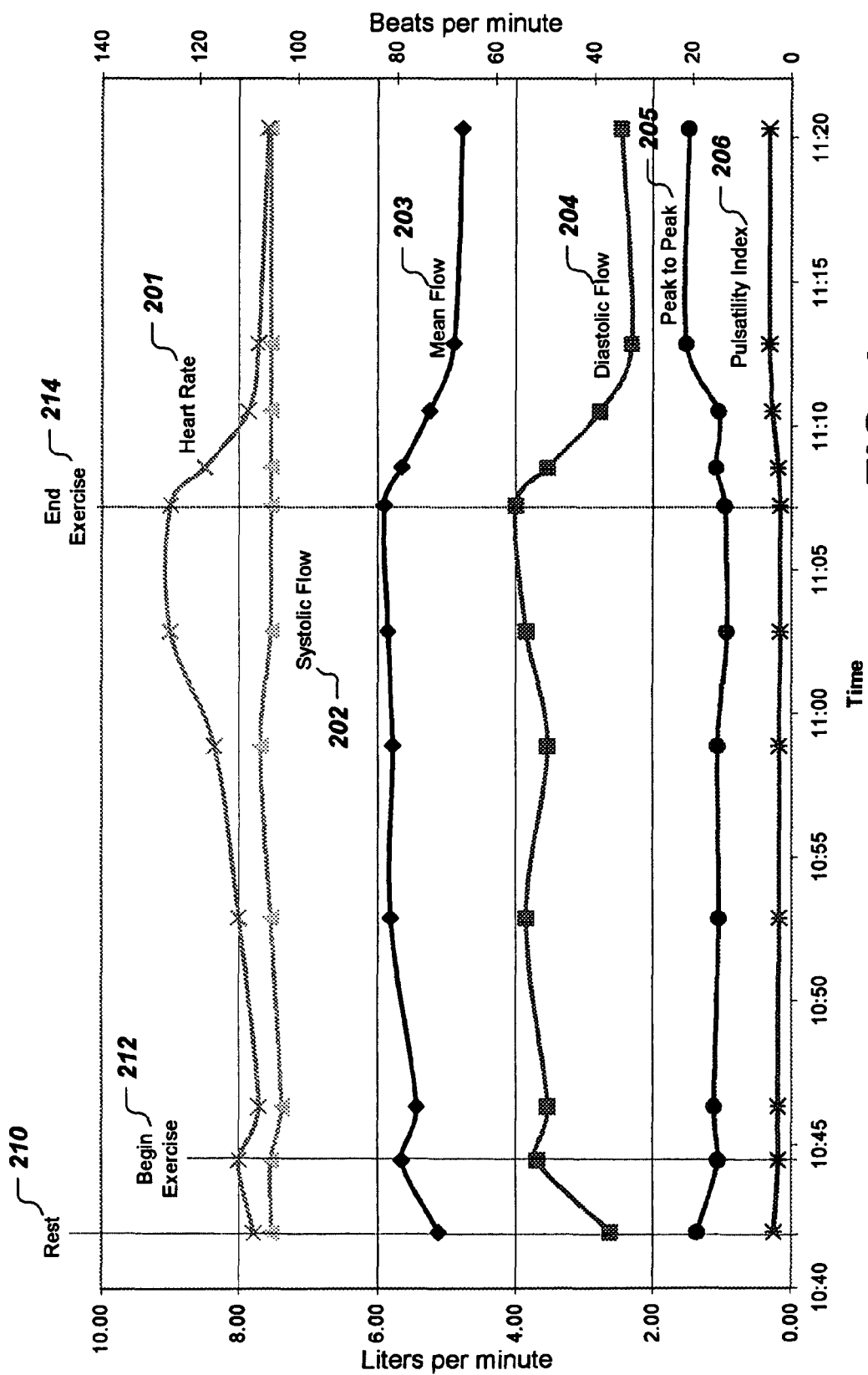
FIG. 4 is a chart illustrating time plots of various physiologic parameters, showing the various parameters' responses to the onset and conclusion of exercise.

FIG. 4 provides time plots of various physiologic parameters, including heart rate 201, peak systolic VAD flow rate 202, mean VAD flow rate 203, peak diastolic VAD flow rate 204, average peak to peak VAD flow (VAD flow maximum-VAD flow minimum) 205, and average pulsatility index 206. Each plot includes rest 210, exercise onset 212, and exercise conclusion 214 points for the patient. As shown in FIG. 4, the peak diastolic VAD flow plot 204 shows the greatest change in response to the onset and conclusion of exercise.

Thus, in accordance with embodiments of the invention, the patient's diastolic VAD flow rate is monitored and the controller module 16 is programmed to increase the speed of the pump 12 in response to an increase in diastolic VAD flow, and decrease the pump speed in response to a decrease in diastolic VAD flow. In specific embodiments, the patient's peak diastolic VAD flow rate or average peak diastolic VAD flow rate is monitored and the pump speed is controlled in response thereto.

Figure 5:
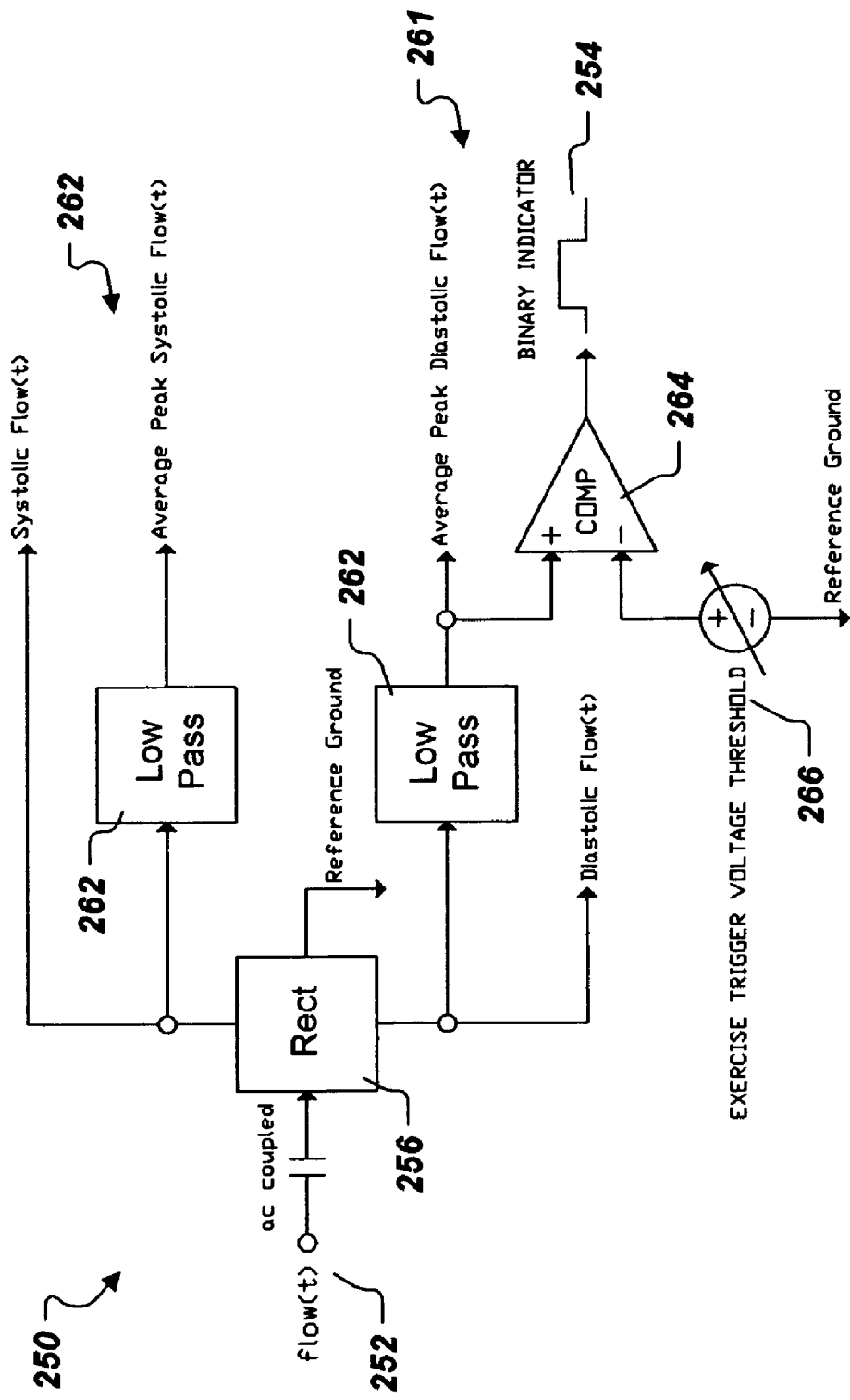
FIG. 5 is a block diagram schematically illustrating a flow processing system in accordance with embodiments of the invention.

FIG. 5 illustrates an analog flow processing system 250 in accordance with an exemplary embodiment of the invention. The system 250 accepts an analog voltage input signal 252 that is proportional to blood VAD flow rate and generates a digital output signal 254 to indicate when a patient has begun/finished exercising.

The VAD flow signal 252 is ac coupled to a precision rectifier 256 to remove the mean VAD flow rate component from the analog VAD flow signal 252. The systolic VAD flow rate 260 and diastolic VAD flow rate 261 are extracted separately. The isolated systolic and diastolic VAD flow signals 260,261 are then low-pass filtered 262 to yield respective average peak values of the systolic and diastolic VAD flow rates. As noted herein, a patient's peak diastolic VAD flow rate or average peak diastolic VAD flow rate increases during exercise and decreases at rest. Thus, peak diastolic VAD flow rate or the average peak diastolic VAD flow rate is applied to a voltage comparator 264 to compare the signal to a predetermined threshold 266 and provide the binary indication 254 of when the patient is exercising. The pump speed may then be adjusted accordingly.

Although the system 250 illustrated in FIG. 5 is based on processing an analog signal proportional to VAD flow rate, it would be a routine undertaking for one skilled in the art having the benefit of this disclosure to apply the same or a similar technique digitally to process VAD flow rate information as discrete sampled data.

As noted herein, heart rate by itself is not believed to be an exclusive physiologic indicator for changing the speed of the pump. However, in exemplary embodiments of the invention, heart rate in combination with diastolic VAD flow rate is used as a physiologic indicator. This provides improved control in patients whose heart rates vary proportionally to their degree of physical activity, while still allowing physiologic control in patients whose heart rate is controlled by medication or by stimulation from a cardiac pacemaker.

In certain embodiments, an increase in the diastolic VAD flow rate or an increase in the heart rate may be used to trigger an increase in pump speed due to an increase in physical activity. However, only a decrease in diastolic VAD flow is used as the indication of a decrease in physical activity resulting in decreasing the speed of the pump 12. The pump 12 is controlled in this manner since it is unknown whether a subsequent decrease in heart rate is the result of a decrease in physical activity or because the speed of the pump 12 had been previously increased. This is because increases in pump speed typically result in a corresponding increase in mean VAD flow rate and thus an increase in the perfusion of oxygen to the body. The patient's native heart rate may therefore decrease (naturally) when the VAD's flow contribution is elevated.

Figure 6:
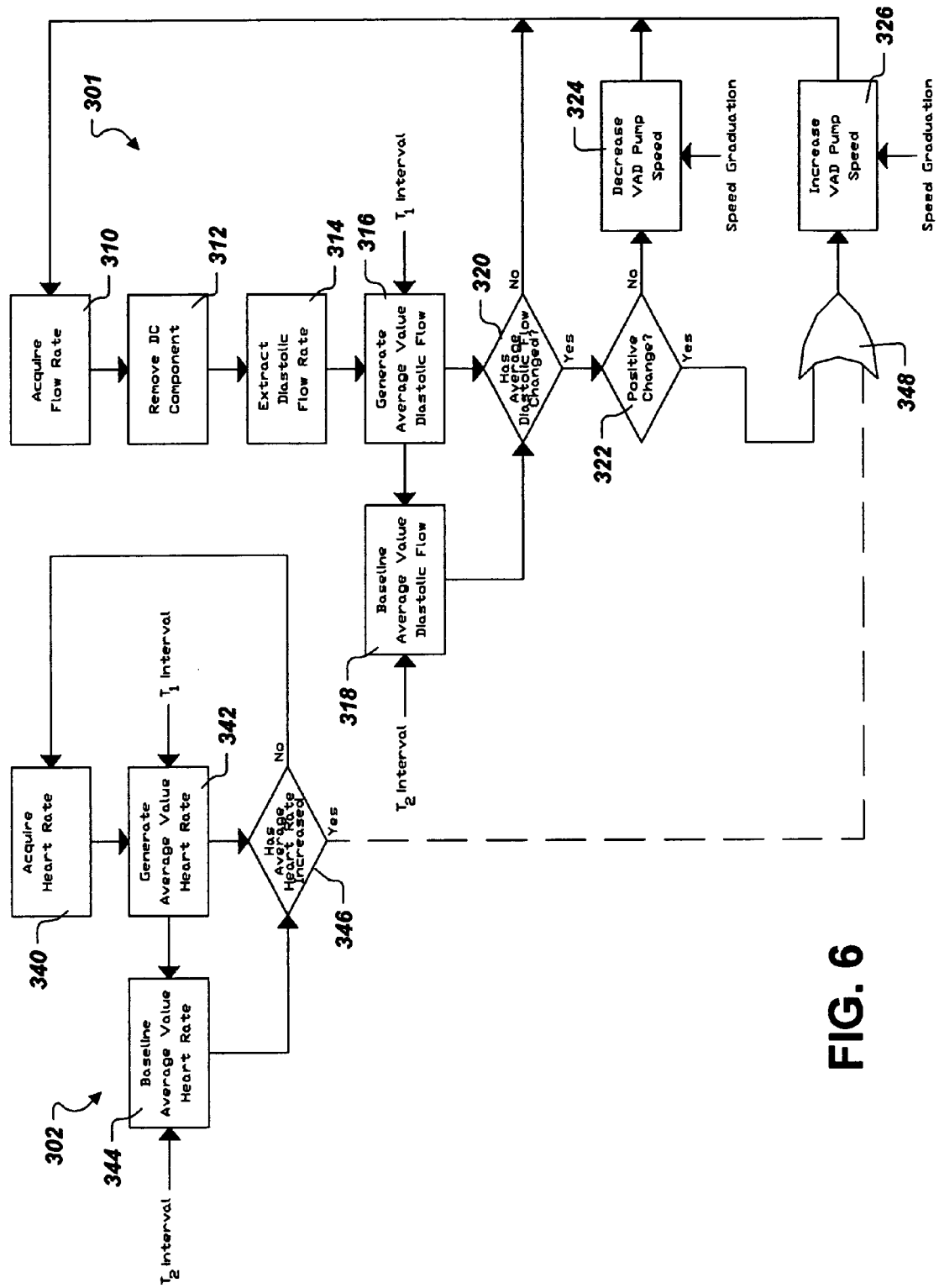
FIG. 6 is a flow diagram illustrating a physiologic control method in accordance with embodiments of the invention.

FIG. 6 is a flow diagram illustrating a physiologic control method in accordance with embodiments of the invention. The illustrated method monitors both diastolic VAD flow 301 (for example, peak diastolic VAD flow rate or average peak diastolic VAD flow rate) and heart rate 302. In block 310, the VAD flow rate is acquired, typically by receiving the VAD flow signal from the flow meter 124. In the particular embodiment illustrated, the flow signal comprises an analog voltage signal that is proportional to the VAD blood flow rate, though other implementations are envisioned in which a digital signal is received. The DC component of the signal is removed in block 312, and the diastolic VAD flow rate is extracted from the flow signal in block 314. This information may be processed in the manner described and illustrated in FIG. 5.

In block 316, the peak diastolic VAD flow rate or average peak diastolic VAD flow rate is computed, and this value is applied to the baseline value in block 318. If the diastolic VAD flow rate has not significantly changed as compared to the baseline (determined in decision block 320), the system continues to monitor the flow information. If the diastolic VAD flow rate has decreased (decision block 322), the pump speed is decreased in block 324 and a new baseline established. If the VAD flow rate has increased, the pump speed is increased in block 326 and a new baseline established.

As noted above, the patient's heart rate may also be monitored, and this information may also be used for physiologic control of the pump. In block 340, the heart rate information is acquired, and the average heart rate (instantaneous heart rate is also applicable) is computed in block 342. The average is applied to the baseline average (block 344). The average heart rate computed in block 342 is compared to the baseline in decision block 346, and if the rate has not increased, the system continues to monitor the heart rate.

If the average heart rate has increased, the pump speed is increased in block 326 and a new baseline established. The outputs of decision blocks 322 and 346 are applied to an OR gate 348, so that if either the heart rate or diastolic VAD flow rate has increased, the pump speed is increased in block 326. However, the pump speed is decreased only in response to a negative change in the diastolic VAD flow rate (block 324).

As noted herein above with reference to FIG. 3, the implantable pump system 10 may include an implantable flow measurement device 14. In embodiments including the implantable flow sensor 14, the flow rate information, and thus the diastolic VAD flow rate information, may be obtained from data the provided by the flow sensor 14 (and flow meter 124 where applicable).

However, the diastolic VAD flow rate information may be obtained through several methods. For example, some embodiments include an implantable pressure sensor, and the pressure data may be used to derive flow rate information. Still further, in other embodiments, other pump signals are monitored and analyzed to extract flow rate information.

The controller 16 receives and monitors various system parameters, such as the pump motor voltage and current (power), the pump speed, flow rate, etc. These signals are time-continuous band-limited signals. The current signal is a composite signal containing the patient's heart rate (assuming the heart is beating) and other frequencies relating to certain physiologic responses within the patient's cardiovascular system such as valve openings and closures, changes in systemic resistance, etc.

The power signal is the product of the pump motor current and pump motor voltage (a constant scalar) and is therefore a composite signal that contains information similar to the current signal. The speed signal typically contains the heart rate of the patient (assuming the heart is beating) as the dominant frequency along with other frequencies related to certain physiologic similar to those discussed above. The flow signal also typically contains the heart rate of the patient and other frequencies related to physiologic responses within the patient's cardiovascular system. Thus, the patient's heart rate information may be extracted from any of several signals available to the controller module 16 for use in a physiologic control scheme.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of controlling a blood pump implanted in a patient, comprising:
    operating the pump at a predetermined speed;
    monitoring the patient's pump flow rate;
    extracting the patient's diastolic pump flow rate from the pump flow rate, wherein the diastolic pump flow rate is a separately isolated flow contribution below a mean pump flow rate; and
    changing the predetermined speed in response to the diastolic pump flow rate, wherein changing the predetermined speed includes increasing the pump speed in response to an increase in the diastolic pump flow rate.

2. The method of claim 1, further comprising:
    monitoring the patient's heart rate; and
    changing the predetermined speed in response to the heart rate.

3. The method of claim 2, wherein changing the predetermined speed includes increasing the pump speed in response to an increase in the heart rate.

4. The method of claim 2, wherein changing the predetermined speed includes increasing the pump speed in response to an increase in the diastolic pump flow rate.

5. The method of claim 2, wherein changing the predetermined speed includes decreasing the pump speed in response to a decreasing in the heart rate.

6. The method of claim 2, wherein changing the predetermined speed includes decreasing the pump speed in response to a decrease in the diastolic pump flow rate.

7. The method of claim 1, wherein changing the predetermined speed includes decreasing the pump speed in response to a decrease in the diastolic pump flow rate.

8. The method of claim 1, further comprising:
    setting the predetermined speed of the pump in accordance with activities performed by the patient.

9. The method of claim 8, wherein the activities are sleeping, normal activity or high energy exertion.

10. A pump system, comprising:
    a pump; and
    a controller having an input for receiving a blood pump flow rate signal, the controller being programmed to extract a separate diastolic pump flow rate from the blood pump flow rate signal and provide a control signal to the pump to vary the speed of the pump in response to the separate diastolic pump flow rate, wherein the separate diastolic pump flow rate is a flow contribution below a mean flow rate.

11. The pump system of claim 10, further comprising an implantable flow measurement device having an output for providing the flow rate signal.

12. The pump system of claim 10, wherein the controller is further programmed to vary the speed of the pump in response to heart rate changes.

13. The pump system of claim 12, wherein the controller is programmed to increase the speed of the pump in response to an increase in at least one of the separate diastolic pump flow rate or the heart rate.

14. The pump system of claim 13, wherein the controller is programmed to decrease the speed of the pump in response to a decrease in the separate diastolic pump flow rate.

15. The pump system of claim 10, wherein the controller is programmed to increase the speed of the pump in response to an increase in the separate diastolic pump flow rate.

16. The pump system of claim 10, wherein the controller is programmed to decrease the speed of the pump in response to a decrease in the separate diastolic pump flow rate.

17. The pump system of claim 10, further comprising an implantable pressure sensor for providing pressure sensor data to the controller.

18. The pump system of claim 17, wherein the pressure sensor data from the pressure sensor is used to derive separate diastolic pump flow rate information.

19. A method of controlling a blood pump implanted in a patient, comprising:
    monitoring the patient's blood pump flow rate;
    extracting the patient's diastolic pump flow rate from the pump flow rate, wherein the diastolic pump flow rate is a separately isolated flow contribution below a mean flow rate;
    changing a speed of the pump in response to the extracted diastolic pump flow rate; and increasing the speed of the pump in response to an increase in the extracted diastolic pump flow rate.

20. The method of claim 19, further including the step of decreasing the speed of the pump in response to a decrease in the extracted diastolic pump flow rate.

* * * * *